US00PP31297P2

(12) United States Plant Patent
Neal, III et al.

(10) Patent No.: US PP31,297 P2
(45) Date of Patent: Dec. 31, 2019

(54) ***THUJA* PLANT NAMED 'T P X T S JUNIOR GIANT'**

(50) Latin Name: ***Thuja plicata* x *Thuja standishii***
Varietal Denomination: T p x T s Junior Giant

(71) Applicant: Hermitage Farms Nursery, Franktown, VA (US)

(72) Inventors: William K. Neal, III, Franktown, VA (US); Stuart F. S. Burnley, Willis Wharf, VA (US)

(73) Assignee: HERMITAGE FARMS NURSERY, Franktown, VA (US)

( * ) Notice: Subject to any disclaimer, the term of this patent is extended or adjusted under 35 U.S.C. 154(b) by 0 days.

(21) Appl. No.: 16/350,361

(22) Filed: Nov. 6, 2018

(51) Int. Cl.
*A01H 7/00* (2006.01)
*A01H 6/00* (2018.01)

(52) U.S. Cl.
USPC ..... Plt./213

(58) Field of Classification Search
USPC ..... Plt./213
CPC ... A01H 7/00; A01H 5/00; A01H 5/02; A01H 5/04; A01H 5/025; A01H 6/00; A01H 6/14
See application file for complete search history.

(56) References Cited

U.S. PATENT DOCUMENTS

PP26,684 P3 * 5/2016 Case, Jr. ..... Plt./213

* cited by examiner

*Primary Examiner* — June Hwu
(74) *Attorney, Agent, or Firm* — Penny J. Aguirre

(57) ABSTRACT

A new cultivar of *Thuja* named 'T p x Ts Junior Giant' that is characterized by its small plant height and width, its small leaves, its dark green foliage, dense growth habit, and its slow growth rate.

2 Drawing Sheets

Botanical classification: *Thuja plicata* x *Thuja standishii*.
Varietal denomination: 'T p x T s Junior Giant'.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1).

BACKGROUND OF THE INVENTION

The present invention relates to a new and distinct cultivar of *Thuja plicata* x *Thuja standishii* and will be referred to hereafter by its cultivar name, 'T p x T s Junior Giant'. 'T p x T s Junior Giant' represents a new cultivar of arborvitae, an evergreen tree grown for landscape use.

The Inventors discovered 'T p x T s Junior Giant' as a naturally occurring branch mutation of *Thuja* 'Green Giant' (not patented) that was growing outdoors in a container at a nursery in 2004 in Franktown, Va.

Asexual propagation of the new cultivar was first accomplished by one of the Inventors using stem cuttings in Franktown, Va. in 2006. Asexual propagation by stem cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'T p x T s Junior Giant' as a unique cultivar of *Thuja*.

1. 'T p x T s Junior Giant' exhibits a small plant height and width.
2. 'T p x T s Junior Giant' exhibits small leaves.
3. 'T p x T s Junior Giant' exhibits dark green foliage.
4. 'T p x T s Junior Giant' exhibits a dense growth habit.
5. 'T p x T s Junior Giant' exhibits a slow growing rate.

The parent plant of 'T p x T s Junior Giant', 'Green Giant', differs from 'T p x T s Junior Giant' in having a larger plant height (about 40% larger), faster growing habit, foliage that is lighter green in color, larger leaves, and a less dense growth habit. 'T p x T s Junior Giant' can be most closely compared to the *Thuja* cultivar 'BFC68' also known as Virginian (U.S. Plant Pat. No. 26,684). Virginian is similar to 'T p x T s Junior Giant' in leaf type and the plant shape. Virginian differs from 'T p x T s Junior Giant' in having leaves that are larger in size, foliage that is lighter in color, and in having a less dense growth habit with branches and leaves that are held more horizontal.

BRIEF DESCRIPTION OF THE DRAWINGS

The accompanying colored photographs illustrate the overall appearance and distinct characteristics of the new *Thuja*. The photographs were taken of a three-year-old plants as grown outdoors in a 3-gallon containers in Franktown, Va.

Figure 1:
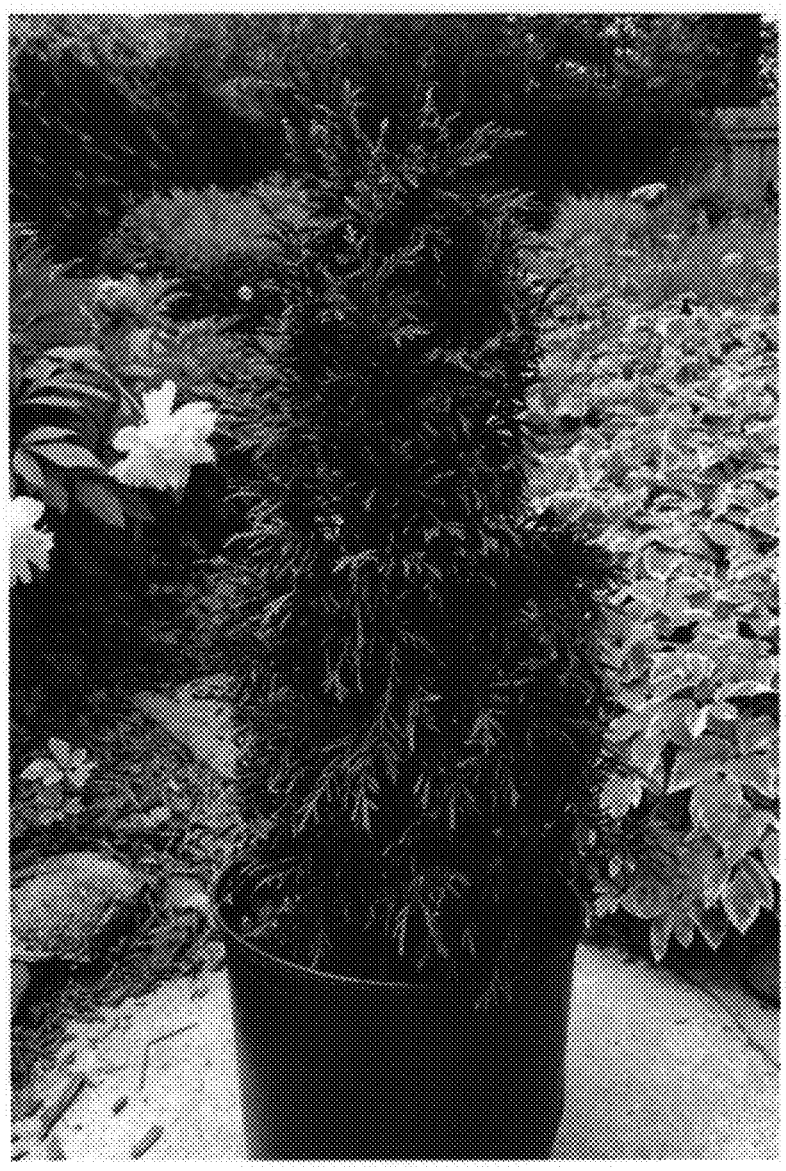
FIG. 1 provides an overall view of the plant habit of 'T p x T s Junior Giant'.
Figure 2:
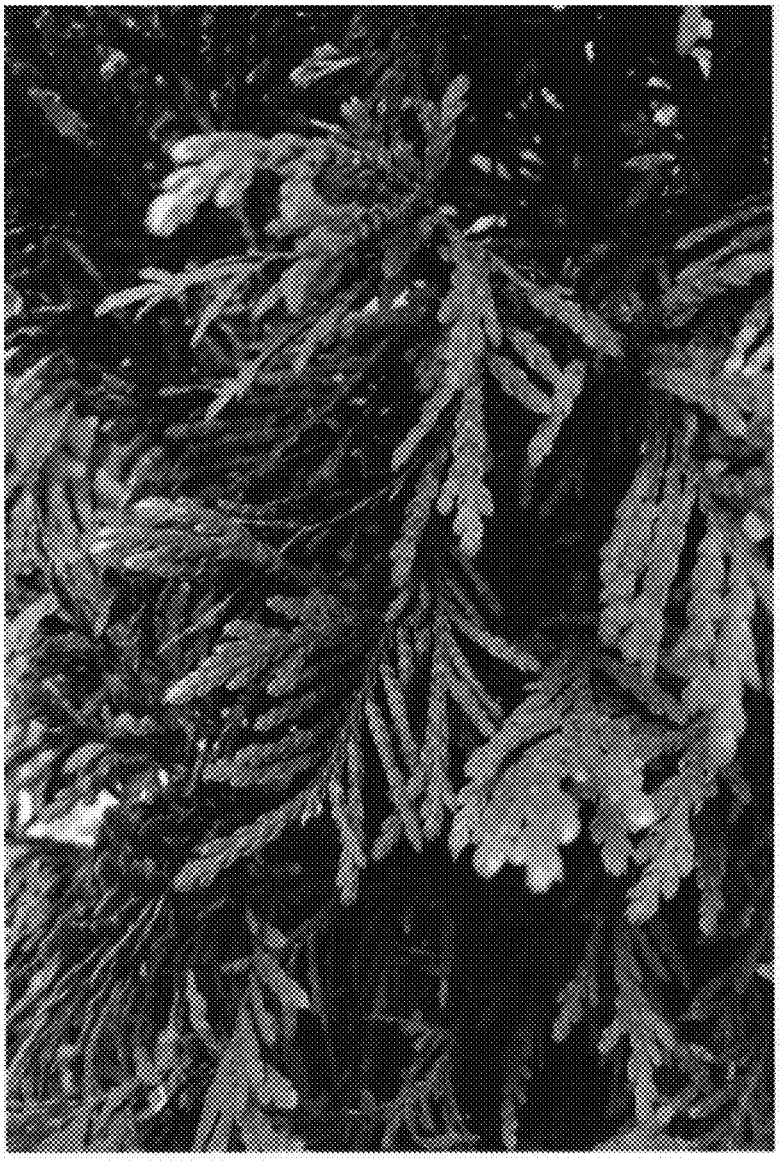
FIG. 2 provides a close-up view of the foliage of 'T p x T s Junior Giant'.

The colors in the photographs are as close as possible with the photographic and printing technology utilized and the color values cited in the detailed botanical description accurately describe the colors of the new *Thuja*.

DETAILED BOTANICAL DESCRIPTION

The following is a detailed description of the new cultivar as taken from three-year-old plants as grown outdoors in 3-gallon containers in Franktown, Va. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Coniferous, evergreen tree.

*Plant habit*.—Narrow conical, upright and compact.

*Plant size*.—An average of 65 cm in height, 27 cm in width as a three year-old plant in a 3-gallon container, 60% smaller in height than the parent plant 'Green Giant.

*Cold hardiness*.—At least to U.S.D.A. Zone 4.

*Diseases and pests*.—No resistance or susceptibility to diseases or pests has been observed.

*Root description*.—Fibrous, moderately branched, moderately thick, 175A in color.

*Propagation*.—Stem cuttings.

*Growth rate*.—Moderately vigorous.

*Root development*.—Roots initiate in about 60 days, a fully rooted plant in a one-gallon container can be produced in one growing season.

Branch description:

*Branch quantity*.—Average of 22 branches from main stem, with 8 to 10 branches per lateral branch.

*Branch shape*.—Rounded.

*Branch size*.—Main branch; 2 cm in width, 50 cm in length, lateral branches; 20 cm in length and 8 mm in diameter, tertiary branches; 18 cm in length, 4 mm in width.

*Branch surface*.—Densely covered with scale-like leaves that are slightly glossy to matte and glabrous, scale-like leaves; whorled in group of 2 to 4 leaves per whorl, 12 per 2 cm section, average of 6 mm in length, 3 mm in width, sharp acuminate apex, color when young is 142A, margins and apex 139A turning to a blend of 164A and 165A when mature and dry, older bark is shiny and with a slightly ripped surface.

*Branch arrangement*.—Alternate.

*Branch strength*.—Strong.

*Internode length*.—Average of 2 cm.

*Branch color*.—Young and mature branches; match branch surface description, older bark; 200A to N200B.

Foliage description:

*Leaf arrangement*.—Alternate.

*Leaf attachment*.—Sessile.

*Leaf shape*.—Linear, scale-like.

*Leaf division*.—Simple.

*Leaf base*.—Cuneate.

*Leaf apex*.—Short apiculate.

*Leaf venation*.—Not distinguishable, coloration matches leaf coloration.

*Leaf margins*.—Entire.

*Leaf fragrance*.—When crushed, scale-like leaves produce a very strong pleasant smell typical fragrance of *Thuja*.

*Leaf surface*.—Upper and lower surfaces; glabrous and glossy.

*Leaf color*.—Immature upper and lower surface; 143A, mature upper and lower surface; NN137A.

*Leaf size*.—Average of 10 cm in length and 3 mm in width.

*Leaf quantity*.—Average of over 10,000 scale-like leaves per branch.

*Leaf glands*.—Average of 0.5 mm in diameter, orbicular in shape, matches leaf color surfaces.

Cone description: Neither male nor female cones have been observed.

It is claimed:

1. A new and distinct cultivar of *Thuja* plant named 'T p x T s Junior Giant' as herein illustrated and described.

* * * * *